(12) United States Patent
Quamar et al.

(10) Patent No.: US 12,019,995 B2
(45) Date of Patent: Jun. 25, 2024

(54) ONTOLOGY-DRIVEN CONVERSATIONAL INTERFACE FOR DATA ANALYSIS

(71) Applicant: INTERNATIONAL BUSINESS MACHINES CORPORATION, Armonk, NY (US)

(72) Inventors: Abdul Quamar, San Jose, CA (US); Robert John Moore, San Jose, CA (US); Dorian Boris Miller, Saratoga, CA (US); Fatma Ozcan, San Jose, CA (US); Jeffrey Thomas Kreulen, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 378 days.

(21) Appl. No.: 16/920,693

(22) Filed: Jul. 4, 2020

(65) Prior Publication Data

US 2022/0004718 A1 Jan. 6, 2022

(51) Int. Cl.
*G06F 40/00* (2020.01)
*G06F 40/279* (2020.01)
(Continued)

(52) U.S. Cl.
CPC ............ *G06F 40/40* (2020.01); *G06F 40/279* (2020.01); *G06N 20/00* (2019.01); *G06Q 40/00* (2013.01); *G16H 50/50* (2018.01)

(58) Field of Classification Search
CPC ...... G06F 40/40; G06F 40/279; G06F 18/214; G06F 40/30; G06F 18/24; G06F 16/9535;
(Continued)

(56) References Cited

U.S. PATENT DOCUMENTS 6,741,959 B1 5/2004 Kaiser
8,935,277 B2 1/2015 Kuchmann-Beauger et al.
(Continued)

OTHER PUBLICATIONS

E. C. Paraiso and J.-.A. Barthes, "SpeechPA: an ontology-based speech interface for personal assistants," IEEE/WIC/ACM International Conference on Intelligent Agent Technology, 2005, pp. 657-663, doi: 10.1109/IAT.2005.128. (Year: 2005).*

(Continued)

*Primary Examiner* — Edgar X Guerra-Erazo
(74) *Attorney, Agent, or Firm* — Intelletek Law Group, PLLC; Gabriel Daniel, Esq.

(57) ABSTRACT

A computer-implemented method for generating an ontology-driven conversational interface includes generating an ontology from a description of a domain schema of a Data Analysis (DA) model, in which the DA model is a defined in terms of quantifiable, qualifying or categorical entities and their relationships as described by the domain schema. Conversational artifacts of a conversation space including a conversational pattern framework are generated by extracting DA-related intents, entities, and a dialog from the generated ontology for the conversational interface. A dialog logic table maps DA-related patterns to intents, extracted quantifiable, qualifying or categorical attributes to entities, and the dialog to user-prompts for one or more parameters in an identified DA pattern. The conversation space is integrated with at least one of an external data source or an analytics platform that stores and processes data.

25 Claims, 17 Drawing Sheets

(51) Int. Cl.
*G06F 40/40* (2020.01)
*G06N 20/00* (2019.01)
*G06Q 40/00* (2023.01)
*G16H 50/50* (2018.01)

(58) Field of Classification Search
CPC .... G06F 30/27; G06F 3/0482; G06F 16/3329; G06F 40/289; G06F 40/295; G06F 16/3344; G06F 3/04842; G06F 40/205; G06F 18/00; G06F 40/20; G06F 2218/08; G06F 40/253; G06F 40/242; G06F 16/90332; G06F 16/288; G06F 40/56; G06F 16/24575; G06F 16/243; G06F 40/268; G06F 40/237; G06F 40/10; G06F 40/00; G06N 20/00; G06N 3/08; G06N 3/045; G06N 3/044; G06N 7/01; G06N 3/04; G06N 5/04; G06N 20/20; G06N 20/10; G06N 5/01; G06N 3/047; G06N 3/048; G06N 5/022; G06N 3/006; G06N 3/02; G06N 5/02; G06N 5/025; G06N 3/0464; G06N 5/046; G06N 3/042; G06N 3/09; G06N 5/045; G06N 3/088; G06N 3/0475; G06N 3/092; G06N 5/00; G06N 3/098; G06N 3/096; G06N 3/094; G06N 3/0895; G06N 3/0985; G16H 50/50; G06Q 40/00; G10L 15/22

See application file for complete search history.

(56) References Cited

U.S. PATENT DOCUMENTS

| | | | |
|---|---|---|---|
| 9,177,047 | B2 | 11/2015 | Xie et al. |
| 9,665,662 | B1 | 5/2017 | Gautam et al. |
| 9,690,848 | B2 | 6/2017 | Thollot |
| 9,984,116 | B2 | 5/2018 | Rais et al. |
| 10,409,846 | B2 | 9/2019 | Schilder et al. |
| 10,528,870 | B2 | 1/2020 | Lindsley |
| 10,719,539 | B2 | 7/2020 | Smith et al. |
| 10,777,191 | B2 | 9/2020 | Shmueli-Scheuer |
| 10,783,188 | B2 | 9/2020 | Wang |
| 2007/0078889 | A1 | 4/2007 | Hoskinson |
| 2010/0057687 | A1 | 3/2010 | Shen et al. |
| 2015/0006432 | A1 | 1/2015 | Grosset et al. |
| 2017/0351962 | A1 | 12/2017 | Appel et al. |
| 2018/0225391 | A1 | 8/2018 | Sali et al. |
| 2018/0373753 | A1* | 12/2018 | Flaks .................... G06F 16/245 |
| 2019/0163782 | A1 | 5/2019 | Drushku |
| 2019/0294693 | A1 | 9/2019 | Kanayama et al. |
| 2019/0354874 | A1 | 11/2019 | Shah et al. |
| 2020/0042642 | A1 | 2/2020 | Bakis et al. |
| 2020/0073984 | A1* | 3/2020 | Sen .................. G06F 16/243 |
| 2020/0143261 | A1* | 5/2020 | Morgan .................. G06N 3/042 |
| 2020/0234177 | A1 | 7/2020 | Matcha et al. |
| 2020/0236068 | A1 | 7/2020 | Tenyenhuis |
| 2020/0265339 | A1 | 8/2020 | Eisenzopf |
| 2020/0327886 | A1 | 10/2020 | Shalaby et al. |
| 2020/0334300 | A1 | 10/2020 | Birnbaum |
| 2020/0334580 | A1 | 10/2020 | Sheopuri |
| 2020/0341976 | A1 | 10/2020 | Aggarwal |
| 2021/0182798 | A1* | 6/2021 | Bikumala ............... G06F 40/30 |
| 2021/0192397 | A1 | 6/2021 | Rastogi et al. |

OTHER PUBLICATIONS

Amith M, Lin R, Cui L, Wang D, Zhu A, Xiong G, Xu H, Roberts K, Tao C. An Ontology-Powered Dialogue Engine For Patient Communication of Vaccines. CEUR Workshop Proc. Oct. 2019;2427:24-30. PMID: 32704245; PMCID: PMC7376741. (Year: 2019).*

Quamar, Abdul & Lei, Chuan & Miller, Dorian & Ozcan, Fatma & Kreulen, Jeffrey & Moore, Robert & Efthymiou, Vasilis. (2020). An Ontology-Based Conversation System for Knowledge Bases. 361-376. 10.1145/3318464.3386139. (Year: 2020).*

Mell, P. et al., "Recommendations of the National Institute of Standards and Technology"; NIST Special Publication 800-145 (2011); 7 pgs.

List of IBM Patents or Patent Applications Treated as Related, 2 pgs.

Hurrell, E. et al., "A Conversational Collaborative Filtering Approach To Recommendation"; Advances in Visual Informatics, (IVIC 2013); Lecture Notes in Computer Science, vol. 8237. Springer, Cham. https://doi.org/10.1007/978-3-319-02958-0_2; 12 pgs.

Quamar, A. et al., "Conversational BI: An Ontology-Driven Conversation System For Business Intelligence Applications", Proceedings of the VLDB Endowment (2020); vol. 13:12, pp. 3369-3381.

Castaldo, N. et al, "Conversational Data Exploration", ICWE (2019), Lecture Notes in Computer Science, vol. 11496, Springer, Cham. https://doi.org/10.1007/978-3-030-19274-7_34, 9 pgs.

Li, R. et al., "Towards Deep Conversational Recommendations", 32nd Conference on Neural Information Processing Systems (NeurIPS 2018), 17 pgs.

Chen, Z. et al., "Towards Explainable Conversational Recommendation", Proceedings of the Twenty-Ninth International Joint Conference on Artificial Intelligence (IJCAI-2020), pp. 2294-3000.

* cited by examiner

1300

1305

- DI Analysis query: Show me {M} by {D} for {V}
  - M: Set of measures
  - D: Set of Dimensions
  - V: Set of filters (instance values for dimensions)
  - E.g. Show me admits (@Measure) by @ Medical Diagnostic Code (MDC: Dimension) for 2017 (Instance for dimension @year)           1307
- Other standard BI patterns:
  - Drill down, Roll up, Pivot           1309
- Ranking (Order By)
  - E.g. Show me top k Admits by MDC
    - Sort order by #Admits
    - Maybe not another intent but add top k as an entity with other examples of how people might specify top k
- Comparisons: Compares two or more measures against each other for a particular dimension and possibly a filter value
  - E.g. What is my C-Section admit rate by hospital compared to normal deliveries
    - Compares #Admits by C-Section delivery vs Normal delivery by facility

ONTOLOGY-DRIVEN CONVERSATIONAL INTERFACE FOR DATA ANALYSIS

BACKGROUND

Technical Field

The present disclosure generally relates to conversational systems, and more particularly, it relates to accessing data by an ontology-driven conversation system.

Description of the Related Art

Conversational interfaces enable a wide range of users, including non-technical personnel, to retrieve data associated with various disciplines. Through the use of natural language, text, and/or speech, such conversational interfaces may provide data in predetermined formats and/or based on anticipated types of user queries.

SUMMARY

According to one embodiment, a computer-implemented method for generating an ontology-driven conversational interface includes generating an ontology from a description of a domain schema of a Data Analysis (DA) model, in which the DA model is defined in terms of quantifiable, qualifying or categorical entities and their relationships as described by the domain schema. The conversational artifacts of a conversation space are generated by extracting DA-related intents, entities, and elements for building a dialog from the generated ontology for the conversational interface. The extracted DA patterns are mapped to DA intents, the extracted quantifiable, qualifying or categorical attributes are mapped to entities and the dialog is mapped to agent-prompts for one or more parameters in an identified DA pattern. The conversation space is integrated with at least one external data source or an analytics platform that stores and processes data.

In one embodiment, the conversational interface transmits a natural language response to a natural language query to access information in the external data source described by the DA model.

In one embodiment, data and visualizations are retrieved from the analytics platform by the conversational space.

In one embodiment, the generated ontology is enriched by providing at least one meta-concept as a grouping of one or more of the quantifiable, qualifying or categorical attributes extracted as entities from the generated ontology.

In one embodiment, the dialog logic table is formed by specifying the one or more parameters associated with each intent, and identifying each of the specified one or more parameters as being optional or required.

In one embodiment, the conversation space includes one or more training samples, and the method further comprises training the conversation interface by machine learning to learn a model to identify an intent in a user utterance.

In one embodiment, the training of the conversation interface is performed using a classification mechanism. The classification mechanism may be a deep neural network.

In one embodiment, a method of generating a conversation space of a conversational interface for a Data Analysis (DA) application includes generating an ontology from a description of a domain schema of a DA model including DA-related quantifiable and categorical entities and relationships between them. The ontology is annotated with semantic information from the DA model. There is a mapping of the DA intents, entities, and the dialog from the ontology to the dialog logic table that includes a quantifiable entity, a categorical attribute, a filter, and a relationship between the mapped components. A generation of conversational artifacts of the conversation space from the ontology is performed from the extracted intents, entities and elements for building a dialog for the conversational interface. The conversation space is integrated with at least one of an external data source or analytics platform to store and process data.

In one embodiment, there is a grouping of the entities from the ontology into one or more meta-concepts and a domain-dependent interpretation of each meta-concept.

In one embodiment, the method further includes forming an ontology graph from the generated ontology. The ontology graph is enhanced by adding one or more of new concepts, groupings, hierarchies, relationships discerned from a data-driven machine learning, a deep learning, an embedding based technique for named entity recognition, or a link prediction. The ontology graph is periodically enhanced, and a subsequent process of generating the conversational artifacts is performed as more data is consumed.

In one embodiment, a set of generic terms are added to the dialog table as synonyms for entities in user utterances.

In one embodiment, the generating of the ontology further includes obtaining a taxonomy or hierarchies from a description of the DA model in terms of parent-child relationships.

In one embodiment, the computer-implemented method includes configuring a generic dialog structure for making a series of complex open requests for one or more DA-related requests including one or more of analytic queries, trend requests, and comparison requests.

In one embodiment, a set of generic operations for one or more DA-related requests is configured for DA, and includes operations to drill down, roll up, and pivot on a previous query.

In one embodiment, an ontology-driven conversational interface of a conversation device includes an intent module configured to identify goals and actions from utterances of a user as one or more intents. An entity module is configured to identify information associated with a user utterance as one or more entities. A dialog module is configured to provide a response to a user based on the identified one or more intents, one or more entities, and a context of a conversation. A processor is configured to generate an ontology from a description of a domain schema of a Data Analysis (DA) model, and to generate one or more conversational artifacts of a conversation space by extraction of DA-related intents, entities and a dialog from the generated ontology for the conversational interface. An analytics platform is configured to store and process data from the conversation space, and to provide responses to user queries using structured query generation, in the form of at least one of charts, visualizations, and audio. The ontology includes at least one meta-concept as a grouping of one or more of the quantifiable or qualifying or categorical attributes associated with the extracted entities of the generated ontology.

In one embodiment, the DA model comprises a cube definition, and the conversational interface includes a training module configured to train for identification of different types of user intent from one or more training samples including user utterances.

In one embodiment, the conversation space is integrated with at least one of an external data source or an analytics platform that stores and processes data.

In one embodiment, the analytics platform comprises one of a healthcare analysis platform, or a finance platform.

In one embodiment, a non-transitory computer-readable storage medium tangibly embodying a computer-readable program code having computer-readable instructions that, when executed, causes a computer device to perform a method for generating an ontology-driven conversational interface, the method includes generating an ontology from a description of a domain schema of a Data Analysis (DA) model, in which the DA model is defined in terms of quantifiable, qualifying or categorical entities and their relationships as described by the domain schema. Conversational artifacts of a conversation space are generated by extracting DA-related intents, entities and elements for building a dialog from the generated ontology for the conversational interface. The conversational interface receives a natural language query to access information in the external data source described by the DA model. The conversational interface transmits a natural language response to the natural language query to access information in the external data source described by the DA model.

In one embodiment, in response to receiving a natural language query to access information in the DA model, the natural language query is parsed to extract query entities and query intents from the natural language query. A plurality of query responses to the natural language query is generated based upon the extracted intents and entities. The computing device ranks the query responses, and the transmitting of the natural language response includes a top-ranked query response to the natural language query.

In one embodiment, extracted DA-related patterns are mapped to intents, the extracted quantifiable and qualifying or categorical attributes are mapped to entities, and the dialog to user-prompts for one or more parameters in an identified DA pattern of the DA patterns. A conversation space is integrated with at least one of an external data source or an analytics platform that stores and processes data. The dialog logic table is formed by specifying for each intent, natural language utterances of a user corresponding to the intent, and agent-prompts for one or more parameters in an identified DA pattern.

In an embodiment, the generated ontology is enriched by providing at least one meta-concept as a grouping of one or more of the quantifiable or qualifying or categorical attributes associated with the extracted entities from the generated ontology. The ontology is annotated with semantic information from the DA model.

In one embodiment, there is a computer-implemented method for prompting a user to provide information missing from a current context in an ontology-driven conversational interface. The method includes clarifying user utterances to the conversational interface that map to specific terms based on one or more of a domain vocabulary, synonyms, a hierarchical meta-concept, and use of default inferences support. The computing device prompts a user for predetermined fields based on a dialog logic table. The user's selection is verified by using an ontology to check parameters in an identified Data Analysis pattern. The user is prompted to provide additional terms from a list of words associated with the identified Data Analysis pattern.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition to or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

FIG. 13 illustrates access patterns regarding analysis queries for data analysis, consistent with an illustrative embodiment.

DETAILED DESCRIPTION

Overview

Figure 1:
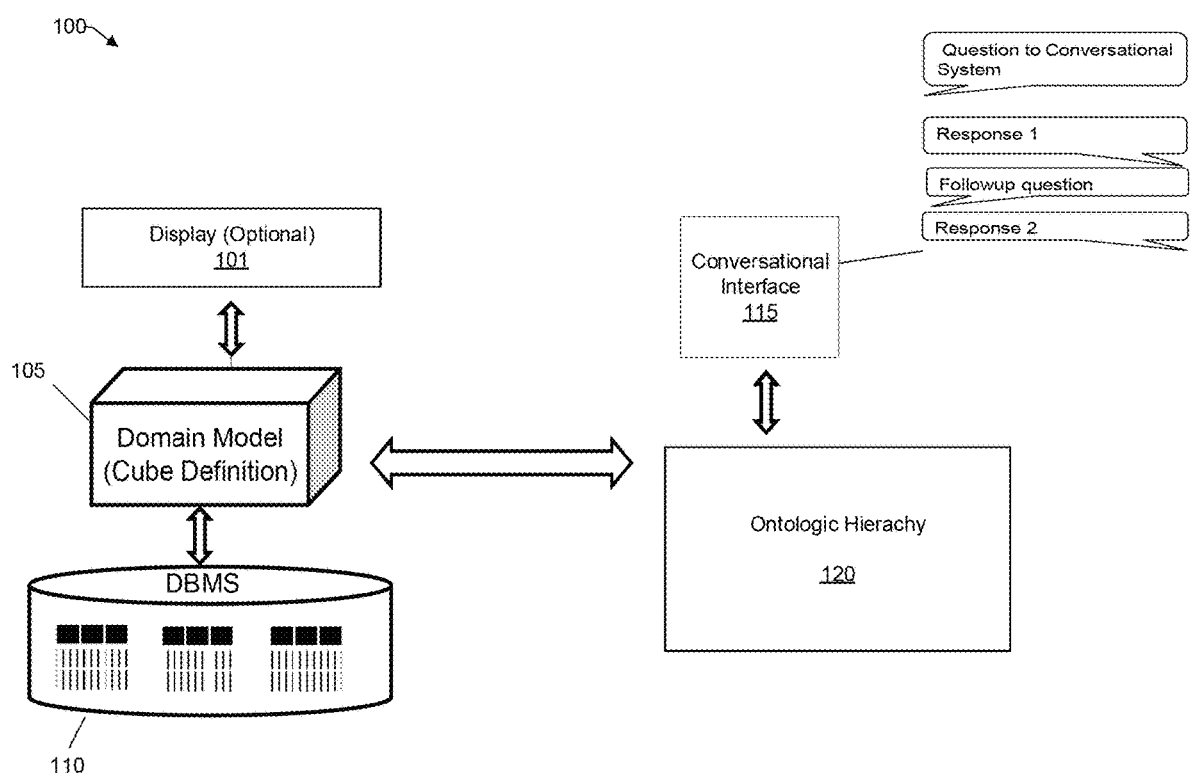
FIG. 1 is a diagram providing an overview of an architecture for an Ontology-Driven Conversational System for Data Analysis (DA), consistent with an Illustrative embodiment.

In the following detailed description, numerous specific details are set forth by way of examples to provide a thorough understanding of the relevant teachings. However, it should be understood that the present teachings may be practiced without such details. In other instances, well-known methods, procedures, components, and/or circuitry have been described at a relatively high-level, without detail, to avoid unnecessarily obscuring aspects of the present teachings.

The term "data analysis," as used in embodiments of this disclosure, refers to a set of tools and applications that assist in analyzing data to glean insights that can be a basis of performing actions to achieve or exceed objectives in various fields, including but not in any way limited to healthcare, manufacturing, pharmaceuticals, engineering, software, transportation, or security. In addition, with regard to the present disclosure, a Natural Conversation Interface (NCI) and a Natural Exchange utilize a persistent context for operation, e.g., turns of conversation. Accordingly, a conversation manager is used to handle activities at the sequence and conversation levels. New queries can be made incrementally based on the conversation context of prior turns of an interaction. When an interaction, (or conversation) is completed, the conversation manager can detach the persistent context. The NCI may use an expandable sequence model that recognizes more types of slots than a conventional slot filling.

In existing interfaces to DA applications, the ability to identify insights regarding data is limited to predefined visualizations through dashboards and Application Program Interfaces (APIs). Users typically manually search for the appropriate charts and decipher information content displayed. Thus, the predetermined ways to analyze data using dashboards does not provide flexibility.

In known chatbots and voice assistant platforms, conversational interfaces (natural language interfaces) can be created for various kinds of domains (e.g., music, weather, healthcare, finance, travel) and are designed to target a range of domain-specific tasks by task-oriented agents. Examples of domain-specific tasks include but are not in any way limited to booking a flight, or finding a drug dosage. However, such task-oriented agents limit the scope of the interaction to a task at hand.

According to the present disclosure, ontology-driven conversational interfaces are configured to enable users with a diverse group of skill sets to explore data and obtain insights about the data without utilizing a dashboard to obtain access to the data. Such ontology-driven conversational interfaces may include but are not limited to chatbots and voice assistant platforms. Moreover, in a conversational data analysis (DA) system supporting conversational interfaces for DA applications, a workload can be defined by a rich set of access patterns against an On-Line Analytical Processing (OLAP) model defined over the underlying data.

In an illustrative embodiment, an ontology is created from a healthcare model defined over raw data. The ontology is in the form that provides rich semantics, reasoning capabilities, and an entity-centric view of the healthcare model which is closer to a natural language conversation. This construction permits greater flexibility in data analysis than the current use of, for example, chatbots and voice assistant platforms that may use a conversational interface to perform the functions of a dashboard.

The computer-implemented method for utilizing a computing device to respond to natural language queries regarding a data analysis according to the present disclosure provides an improvement in fields such as natural language processing, and provides a more dynamic and intuitive conversational interaction to derive DA insights from underlying data in different domains. In addition, the computer-implemented system and method provide for an improvement in the efficiency of computer operations. For example, by virtue of the teachings herein, the improvement in deriving DA insights results in a reduction of the amount of processing power searching the underlying data to provide more accurate responses to natural language queries, as well as reduces the use of computer memory storage.

Example Architecture

FIG. 1 is a diagram 100 providing an overview of an architecture for an Ontology-Driven Conversational System for Data Analysis, consistent with an illustrative embodiment. In one embodiment, an optional display 101 is coupled to a domain model 105. The domain model 105 can include but is not in any way limited to, for example, a healthcare model, a business model, a travel model, a finance model, a weather model, etc., that may be arranged in a cube definition. A database management system (DBMS) 110, which may be a relational DBMS, stores underlying data that will be used to create the domain model 105. In the creation of a domain model 105, a cube definition is a more efficient way to create the domain model from the data because the cube definition provides DA specific information, such as quantifiable, qualifying or categorical attributes, their hierarchies, and how they are related.

A conversational interface 115 is configured to receive queries from a user, and is configured for ontologically—driven retrieval of domain knowledge from the DBMS 110 to provide a response. The conversational system is configurable to provide additional responses to follow-up questions. The response can be provided audibly, visually, audio-visually, or sent to a designated user as a file.

Figure 2:
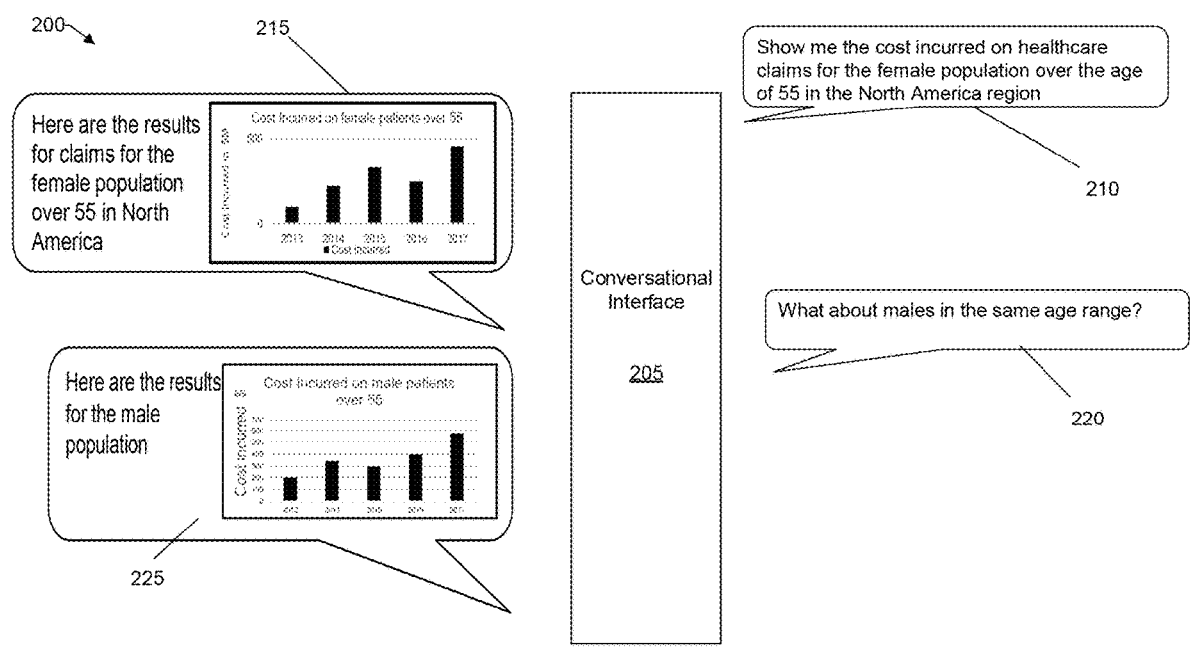
FIG. 2 illustrates an operation of an ontology-driven conversational interface, consistent with an illustrative embodiment.

FIG. 2 illustrates an operation 200 of an ontology-driven conversational interface 205, consistent with an illustrative embodiment. It is to be understood that although the conversational interface is shown to be configured to provide healthcare information for illustrative purposes, the present disclosure is not limited to any particular domain.

At 210, the computer implemented conversational interface 205 receives a query in the form of an audio or text data packet about the cost incurred on healthcare claims for the female population over the age of 55 in North America. At 215, the conversational interface responds, for example, such as according to the architecture shown in FIG. 1. For example, a healthcare domain model may be extracted from a database management system (e.g., DBMS 110). There can be a modeling of the data created by the question asked. Alternatively, if the conversational interface 205 determines that this question was previously asked, a previously created model may be retrieved by the conversational interface 205, and depending on the question, updated to reflect additional data that may have accumulated since the question was previously received by the conversational interface 205. In addition, or alternatively, there may be predefined cube definitions for certain subjects that are supplemented or enhanced with additional data to increase the speed of the response.

The response 215 is shown as a graph with additional language that identifies the question that was asked in the query at 210. However, it is to be understood that the response at 215 is provided for illustrative purposes, and the form of the response is not limited to a type shown as in FIG. 2. For example, there may be only a graphical display, or the information could be provided in a table or list. There could also be links provided for years. As the data retrieved from the DBMS 110 can be formatted in an ontological hierarchy, the response 215 from the conversational interface 205 may include information with more detail provided than received in the query at 210. For example, the graph shows the healthcare costs incurred for female patients over 55 years old for the years 2013-2017. The conversational interface may provide a further breakdown of the patients over 55 years old in, for example, intervals of five years (55-59 years old, 60-64 years old, etc.).

At 220, a follow-up question about males in the same age range is received by the conversational interface 204, and at 225, the conversation interface 205 provides a response based on the follow-up question 220. In FIG. 2, it should be noted that second query 220 did not fully state the question, and the conversational interface 205 provided an ontologically-driven response based on the subject matter of query 210 and the follow-up query 220.

Figure 3:
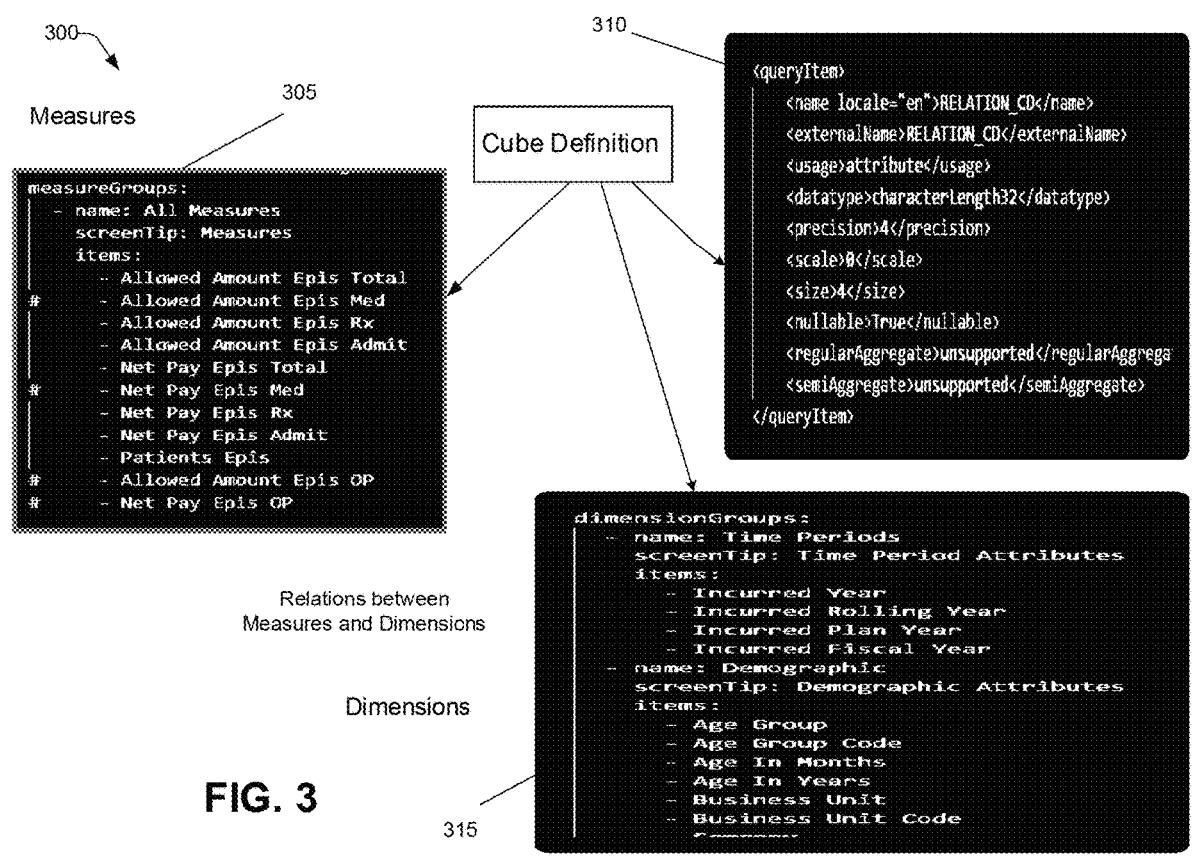
FIG. 3 illustrates an entity-centric modeling of a cube definition, consistent with an illustrative embodiment.

FIG. 3 illustrates an entity-centric modeling 300 of a cube definition defined in terms of quantifiable, qualifying or categorical entities and their relationships as described by the domain schema, consistent with an illustrative embodiment. More particularly, while the embodiment of FIG. 3 shows the use of measures and dimensions for the cube definition, it is to be understood that the use of measures and dimensions is provided for illustrative purposes and the present disclosure is not limited by this illustrative embodiment. In the example of FIG. 3, a DA ontology is shown for a financial ontology, however, as previously mentioned, any domain model including but not limited in any way to healthcare, travel, music weather, etc., can be modeled. The cube definition 301 includes groups of quantifiable entities 305(e.g., which can include but is not limited to measures), query items 310, and groups of qualifying or categorical attributes (e.g., which can include but is not limited to dimensions). For example, the groups of qualifying or categorical attributes 305 correspond to quantifiable elements computed over one or more elements in the physical schema (e.g., columns in a relational schema). The ontology captures the quantifiable and qualifying or categorical attributes defined in the model as entities, their taxonomy or hierarchies are obtained from the cube-definition in terms of parent-child relationships. The capturing of the quantifiable, qualifying or categorical attribute hierarchy and the relationships between allow for effective modeling of the particular domain and basic operations such as drilling down, rolling up and pivot.

Figure 4:
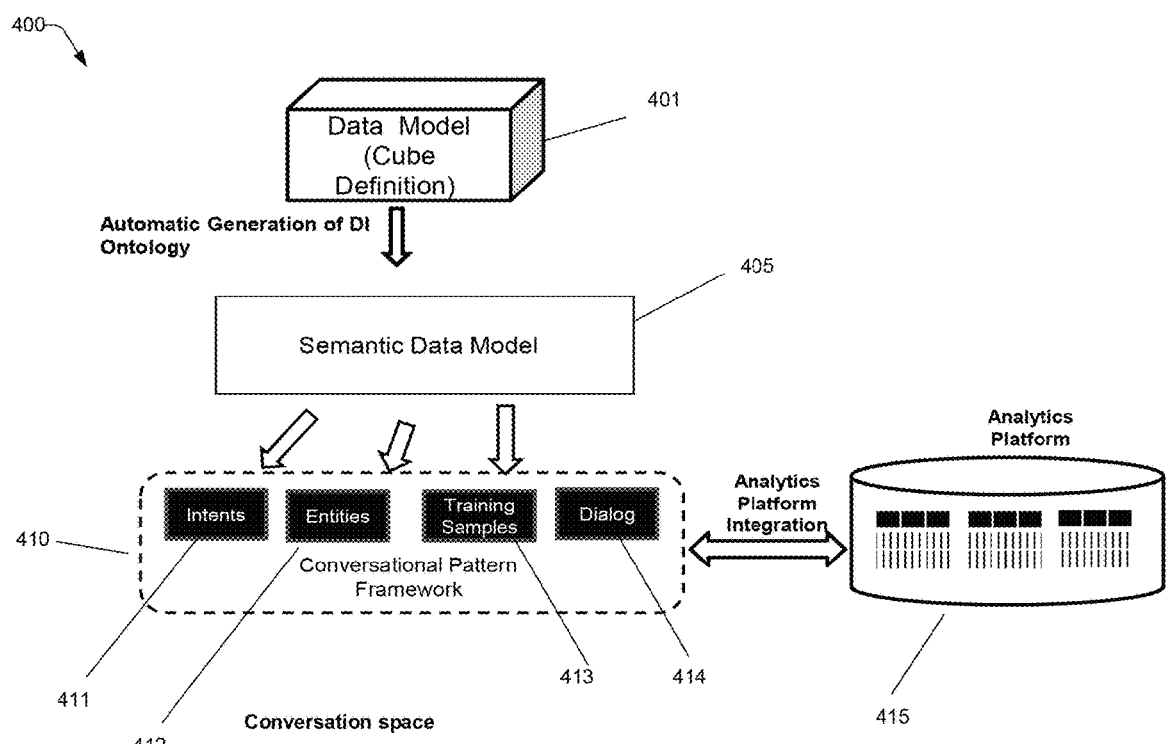
FIG. 4 illustrates an ontology-driven generative approach for a Conversational DA, consistent with an illustrative embodiment.

FIG. 4 illustrates an ontology-driven approach 400 for generating a Conversational Interface according to an illustrative embodiment. The data model 401 is defined over raw data in the form of an ontology providing rich semantics, reasoning capabilities and an entity-centric view of the data model that is closer to a natural language conversation. The ontology is configured to provide a formalism to capture and represent the content and structure in the data model. The ontology represents a central repository for capturing the domain schema and any variations over time, rendering a more dynamic and adaptable system. As discussed above, the ontology captures the quantifiable and qualifying or categorical attributes defined in the data model as entities, and their taxonomy or hierarchies in terms of parent-child relationships. In addition to the ontology capturing the individual relationships between the quantifiable entities, and the qualifying or categorical attributes, special concepts in the ontology are referred to as meta-concepts. Meta-concepts represent a higher-level grouping of quantifiable entities/qualifying or categorical attributes identified from underlying data by machine learning, or deep learning techniques, all of which may be referred to as "ontology enrichment." Meta-concepts permit reasoning at a semantically higher level and supports the querying of a wider range of personas.

With continued reference to FIG. 4, an automated workflow is used to provide rapid prototyping and system development in different domains. In an embodiment, a first operation includes the generation of the ontology from the data model 401. For example, a semantic data model 405 can be created. It is to be understood that the semantic data model 405 may be directed to various subjects, including but in no way limited to a healthcare model, a finance model, a music model, a weather model, etc. In a second operation, the information captured/modeled in the ontology is used to drive the generation of the required artifact/components of a conversation space 410. Three main components of the conversation space 410 include intents 411, entities 412, and dialog 414. The intents 411 are goals and actions that can be expressed in user utterances. Entities 412 represent information that is relevant to a user's purpose. A classifier or a deep neural network may be used to identify the intent in a user utterance, and training by the use of training sample 413 including user utterances for each type of intent. The dialog 414 component provides a response to a user based on the identified intents, and the entities in the user's input and the current context of the conversation. After the performance of the above-described operations, there is performed an integration of the conversation space with an external data source, or with an analytics platform 415 that stores and processes the data. The integration is achieved through a structured query generation against the analytics platform 415 to enable the conversation system to respond to user utterances with insight in the form of, for example, charts/visualizations.

Figure 5:
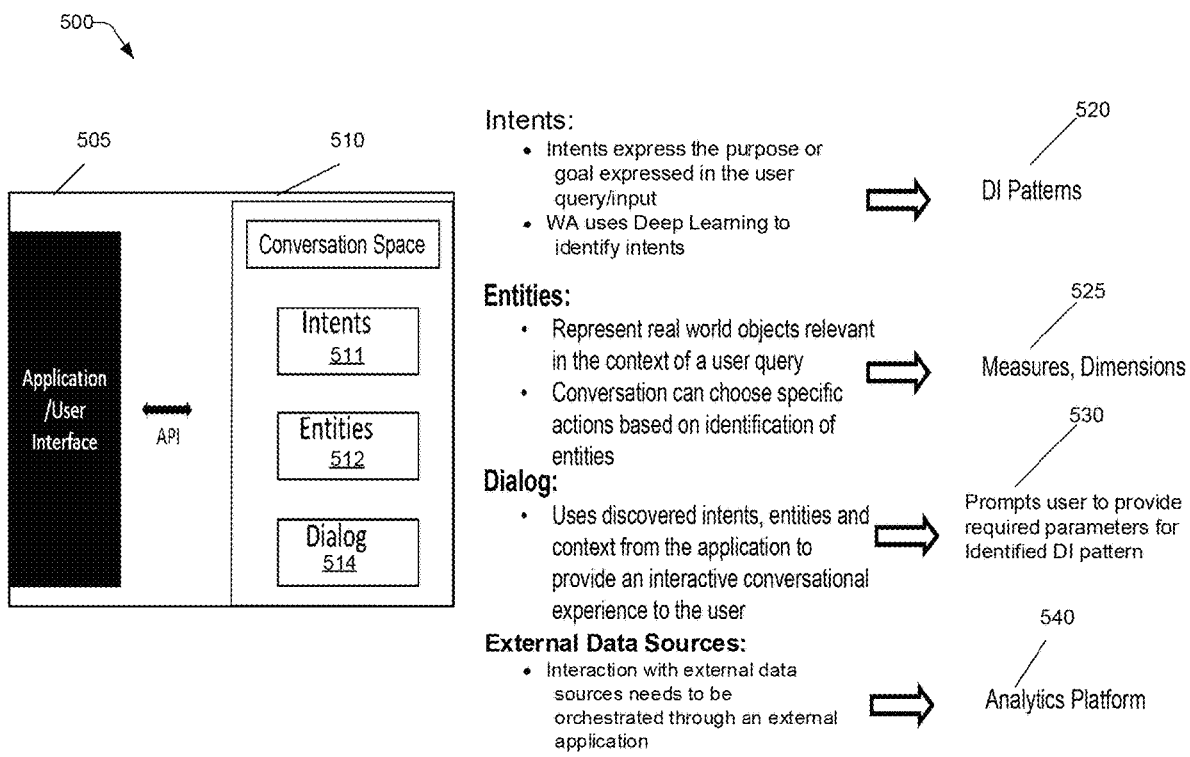
FIG. 5 shows artifacts utilized for constructing a conversation space that is mapped to specific elements of the DA, consistent with an illustrative embodiment.

FIG. 5 is an illustration 500 of the artifacts utilized for constructing a conversation space is mapped to specific elements of the DA consistent with an illustrative embodiment. As shown in 500, there is an Application/User Interface (API) 505 and a conversation space (e.g., space). The Intents 511 capture the purpose or goal in the user query/input. Deep learning can be used to identify intents. It is shown in FIG. 5 that the intents 511 are mapped to the DA patterns 520 These patterns are observed in the user utterances, and are mapped to intents in the conversation space.

The entities 512 represent real-world objects relevant in the context of a user query. A conversational system can be configured to select specific actions based on an identification of the entities 512. A shown in FIG. 5, the entities 512 are mapped to the quantifiable entities and the qualifying or categorical attributes 525. The DA queries involving the quantifiable entities and the qualifying or categorical attributes in the ontology are mapped to appropriate structured queries against an external data source to provide the required response.

As shown in FIG. 5, the dialog 514 uses discovered intents, entities, and context from the application to provide an interactive conversational experience to the user. The dialog 514 is mapped to prompting the user to provide the required parameters for an identified DA pattern. The interaction with external data sources is orchestrated through an external application such as an analytics platform integration application with an analytic platform 540.

Figure 6:
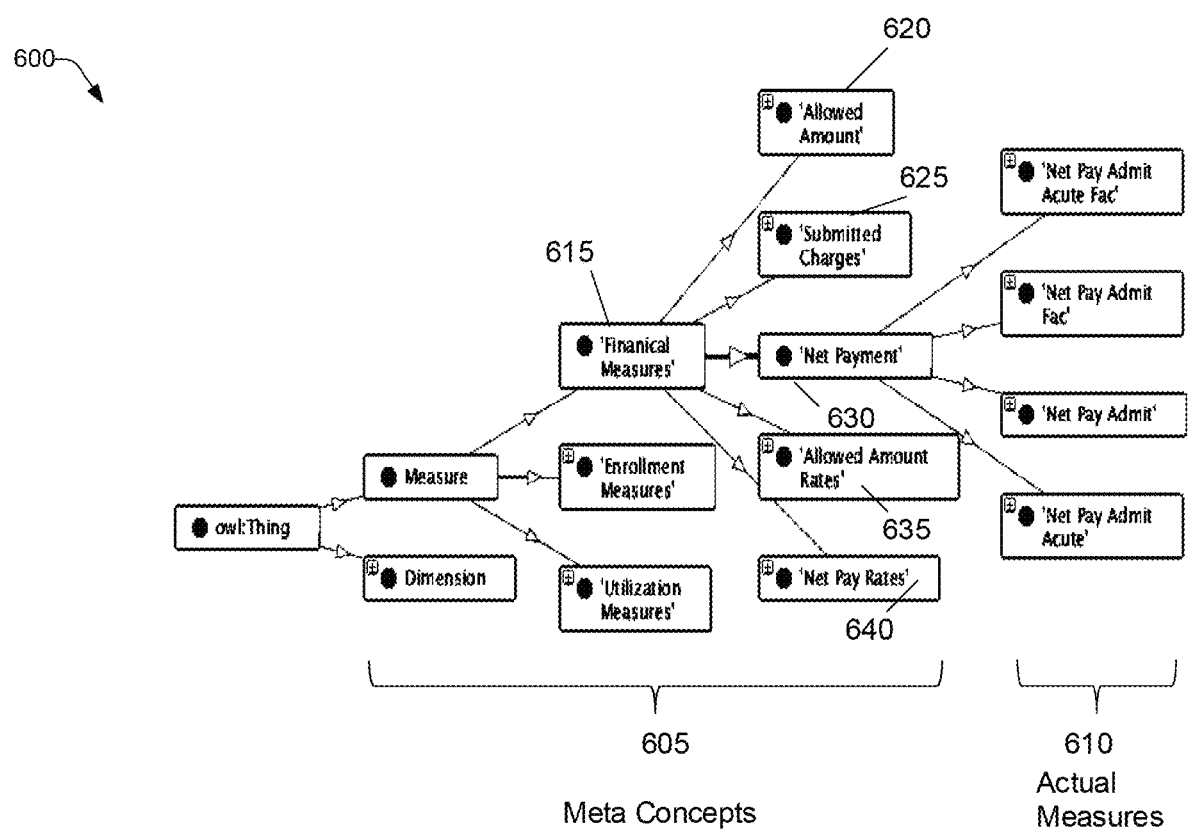
FIG. 6 illustrates a quantifiable entity hierarchy captured in the enriched ontology with annotations for meta-concepts, consistent with an illustrative embodiment.

FIG. 6 illustrates a quantifiable entity (measure) hierarchy 600 captured in the enriched ontology with annotations for meta-concepts, consistent with an illustrative embodiment. In FIG. 6, the enriched ontology is shown in a suite-generated ontology snapshot. The bracketed meta-concepts 605 provide a logical grouping of the measures, and the actual measures 610 are stored in the underlying database. In the particular example illustrated in FIG. 6, the financial measures 615 includes a logical grouping of allowed amounts 620, submitted charges 625, net payments 630, allowed rates 635, and net pay rates 640. In a first approach to measuring intents, for each identified quantifiable entity (measure) in the ontology, an algorithm traverses each edge that connects the measure to a qualifying or categorical attribute. Each pair that is connected via an edge in the ontology is identified as a valid combination.

Alternatively, in a second approach, each individual quantifiable entity may be modeled as a separate intent. Such an approach allows capture of an intent by obtaining information about a measure, irrespective of a qualifying or categorical attribute.

In a third approach, the structural relationships between the measures and dimensions in the ontology are combined with DA workload access patterns from prior user experience and DA application logs. Each identified pattern is modeled as an intent.

Figure 7:
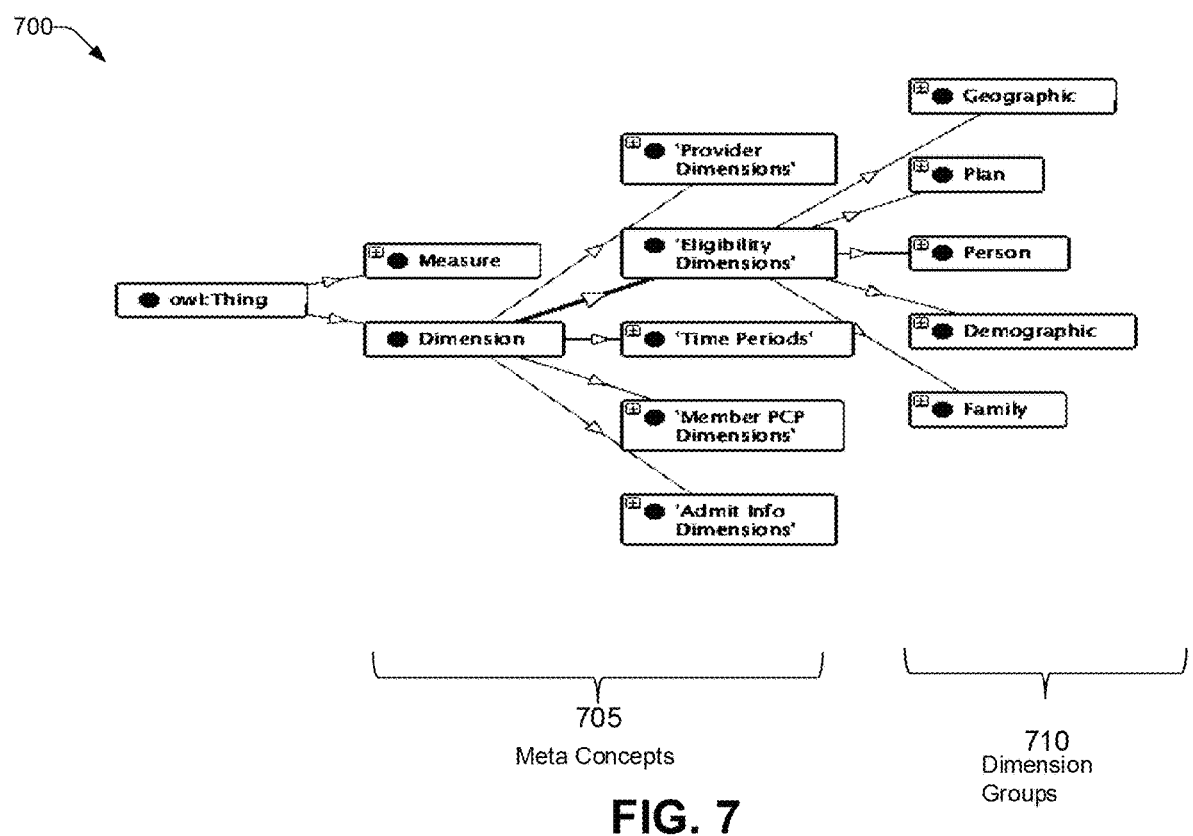
FIG. 7 illustrates a categorical attribute hierarchy captured in the enriched ontology with annotations for meta-concepts, consistent with an illustrative embodiment.

FIG. 7 illustrates a qualifying or categorical attribute hierarchy 700 captured in the enriched ontology with annotations for meta-concepts, consistent with an illustrative embodiment. In FIG. 7, there are grouped meta-concepts 710 and the qualifying or categorical attributes group 715. An algorithm captures the information and models the quantifiable entities, categorical or qualifying attributes, hierarchies, relationships, and other relevant attributes as concepts, data properties, and object properties in a Web Ontology Language (OWL). The meta-concepts provide a logical grouping of the qualifying or categorical attributes that are stored in the underlying database.

Figure 8:
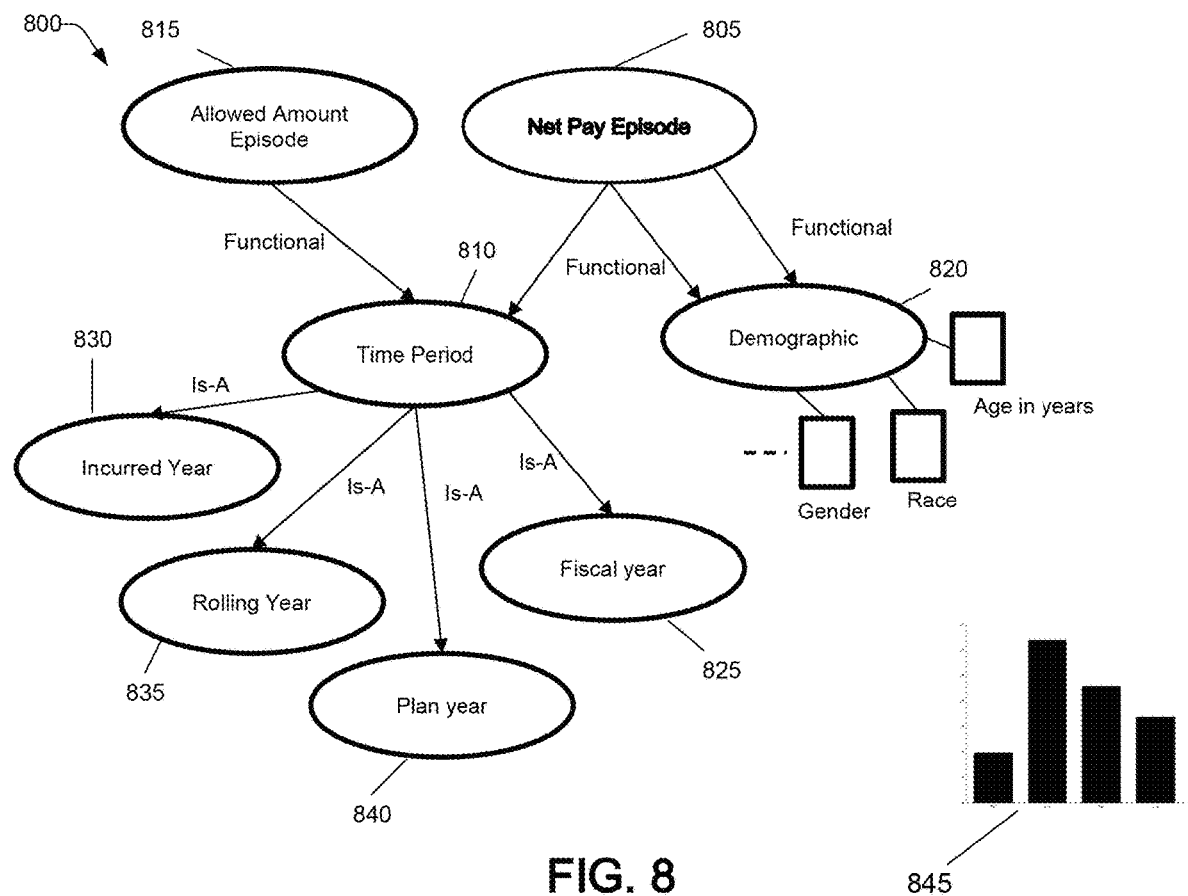
FIG. 8 illustrates a sample question and response, consistent with an illustrative embodiment.

FIG. 8 illustrates a sample question and response 800, consistent with an illustrative embodiment. FIG. 8 illustrates a sample question/utterance "Give me the net pay episode for females by fiscal year." With reference to the conversation space such as shown in FIG. 4, the intent is a DA Analysis Query. The entities include a quantifiable entity, the Net Pay Episode 805. A qualifying or categorical attribute is a time period 810 of a fiscal year 825, and it should be noted that there are other time periods such as the incurred year 830, rolling year 835, and a plan year 840. The filter is a Demographic 820, and the patients are females. The chart displayed in FIG. 8 is the output 845, which is the net pay episode for female patients grouped by fiscal year. Alternatively, the output may also include an alpha-numeric explanation, and an audio-visual response to a user query.

Figure 9:
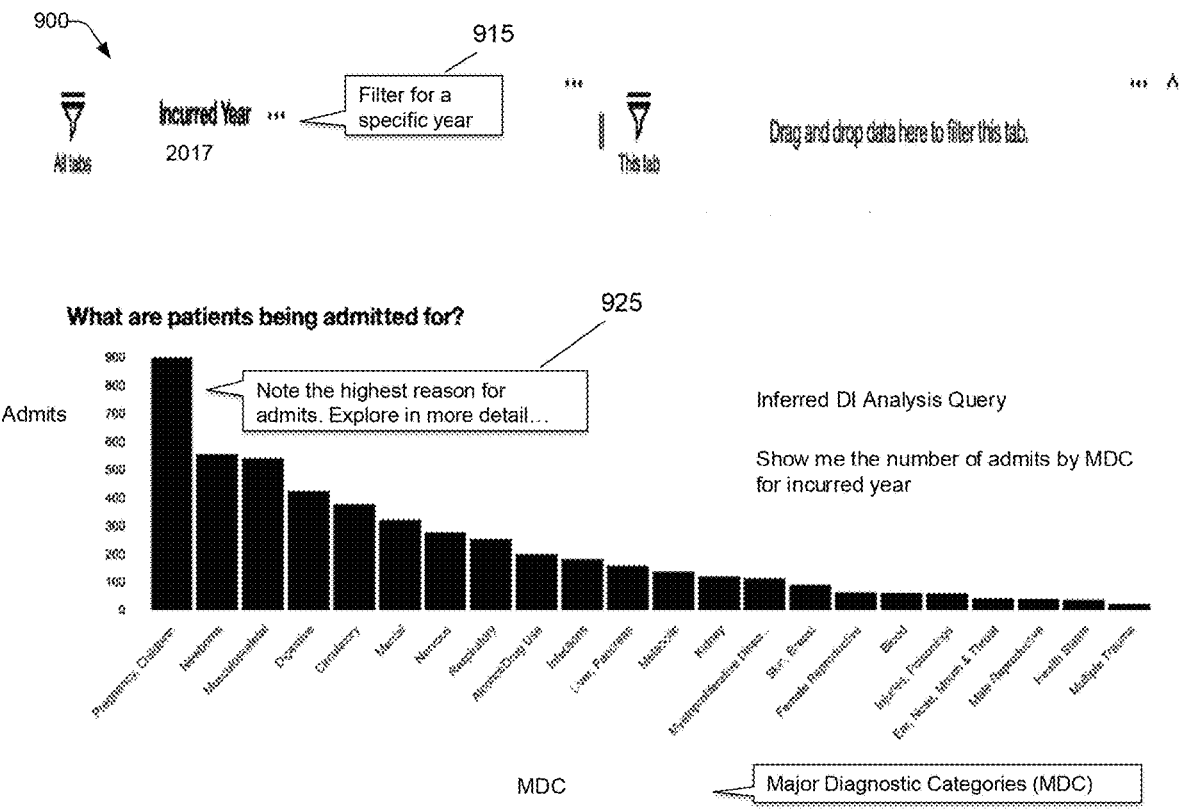
FIG. 9 illustrates a screenshot of a DA analysis query regarding healthcare data, consistent with an illustrative embodiment.

FIG. 9 illustrates a screenshot 900 of a DA analysis query regarding healthcare data, consistent with an illustrative embodiment. A conversational interaction occurs with a conversation interface such as disclosed herein. In the illustrative embodiment, the conversational interface is interacting with an application such as Advantage Suite®. A user asks a question regarding healthcare via the conversational interface. More particularly, the user asks "Show me the number of admits by major diagnostic categories (MDC) for the incurred year." In addition, the above question is qualified with regard to a time period (e.g., a specific year (2017) set by a filter). By operation of an algorithm, which can include, for example, a DA analysis query by sets of quantifiable entities and qualifying or categorical attributes as previously discussed, a graph is output showing the number of admissions for each of the associated major medical diagnostic categories (MDC). At 925, there is a display noting the reason for the largest number of admissions and an option to explore the information in more detail.

Figure 10:
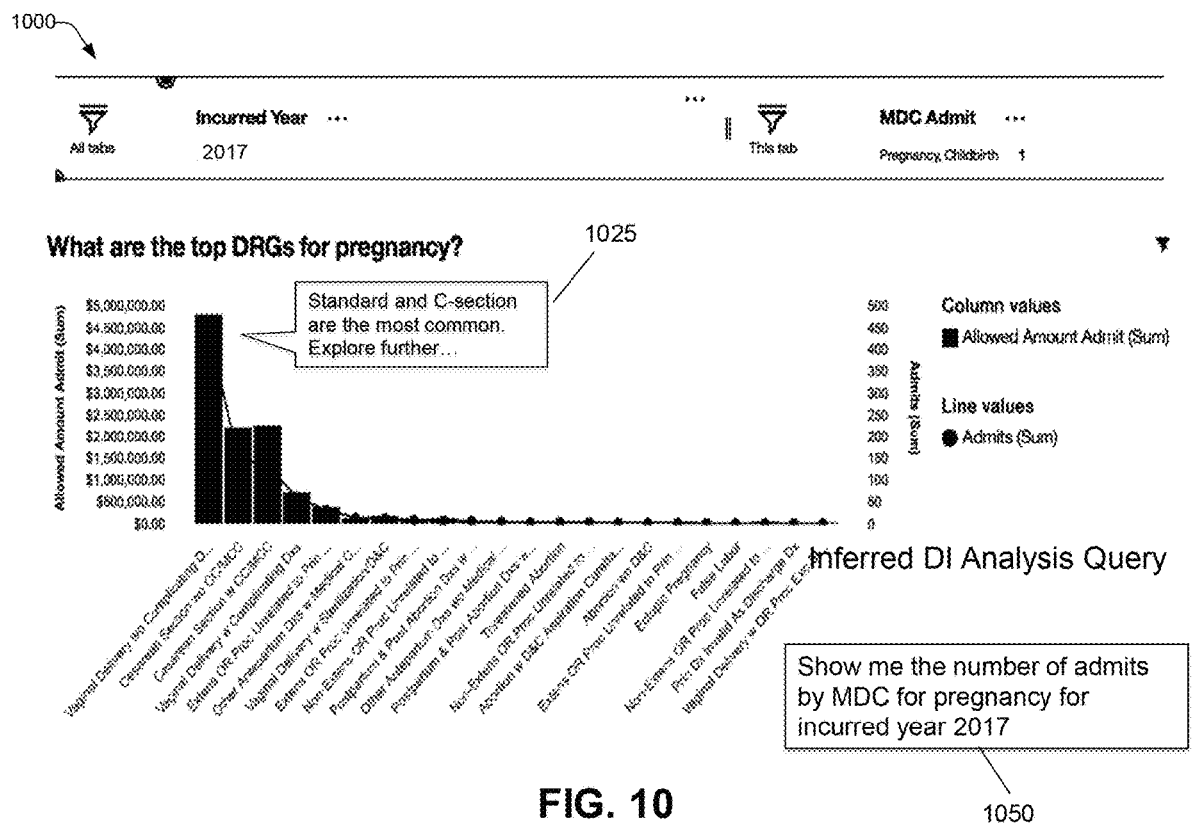
FIG. 10 illustrates a screenshot of a follow-up question of the DA analysis query of FIG. 9, consistent with an illustrative embodiment.

FIG. 10 illustrates a screenshot 1000 of a follow-up question of the DA analysis query of FIG. 9, consistent with an illustrative embodiment. It is shown in FIG. 10 a graph of the top diagnostic related groups (DRG) for the medical conditions 1025 having the highest number of hospital admission in 2017, and their associated healthcare costs each DRG. At 1050, there is shown a DA analysis query to show the number of admits by an MDC.

Figure 11:
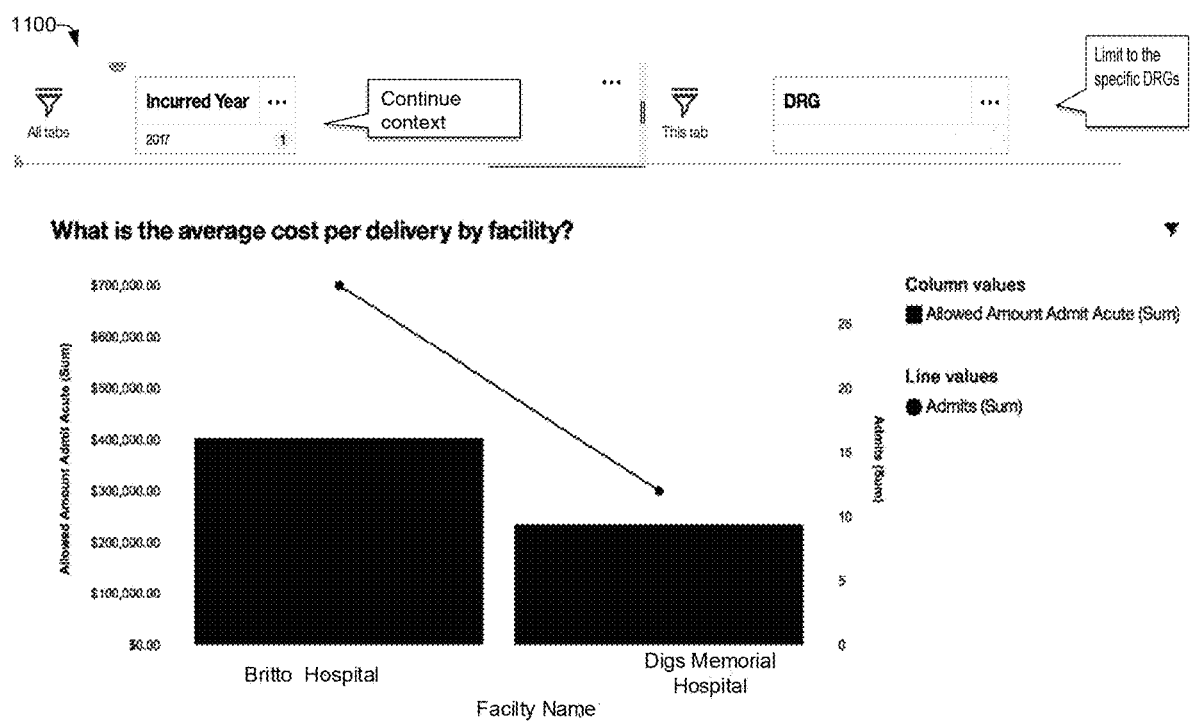
FIG. 11 illustrates a screenshot to another follow-up question of the DA analysis query of FIG. 10, consistent with an illustrative embodiment.

FIG. 11 illustrates a screenshot 1100 to another follow-up question of the DA analysis query of FIG. 9, consistent with an illustrative embodiment. By way of example, FIG. 11 displays the average cost per delivery by facility incurred in 2017.

Figure 12:
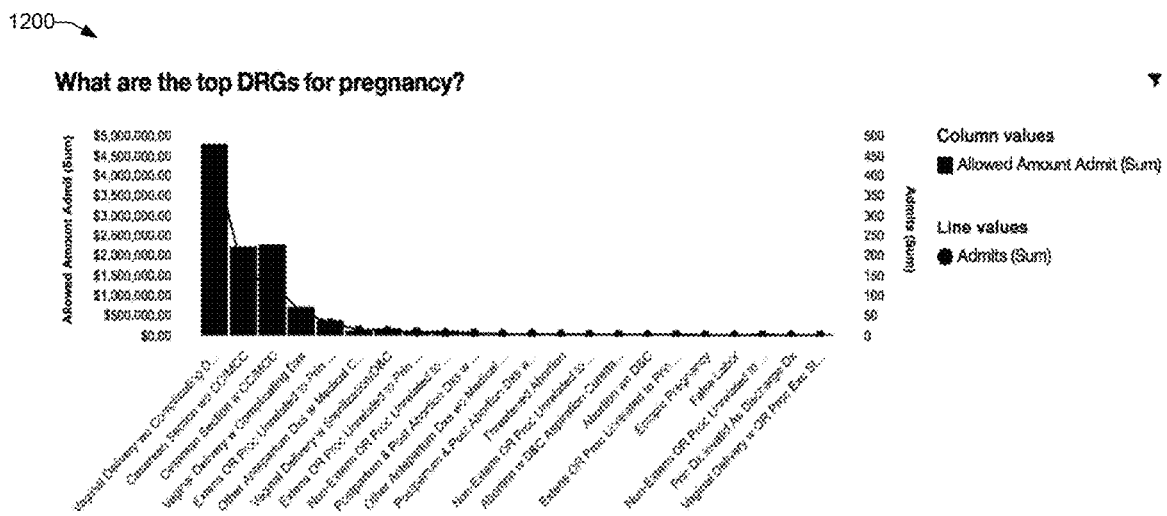
FIG. 12 illustrates the building of a conversational dialog, consistent with an illustrative embodiment.

FIG. 12 illustrates the building of a conversational dialog 1200, consistent with an illustrative embodiment. There is shown a table of example utterances 1205, a request type 1210, a required/assumed qualifying or categorical attributes 1225, and optional qualifying or categorical attributes 1230. The utterance in 1205 is a query regarding what are the DRGs (e.g., qualifying or categorical attributes) by the Allowed amount (e.g., quantifiable entities) by top admits. The DRGs are the qualifying or categorical attribute, and the allowed amount is the quantifiable entity. The request type intent 1210 lists the DA Pattern (e.g., ranking), the quantifiable entity being, for example. admit, and the qualifying or categorical attribute being DRG. In addition, the required/ assumed qualifying or categorical attribute 1225 (e.g., time 2017, or overtime, and MDC admit), and the optional qualifying or categorical attribute 1230 (e.g., allowed amount) are shown.

Moreover, in the building of the conversational dialog, a more efficient conversational thread can be built with fewer follow-up questions through the use of default inferences. For example, the default inferences can provide missing parameters in a query that a user assumes the system would infer given the context of the conversation, without having to respond to a user query with a question to clarify the query, and/or waste computer resources on providing a generalized response to a query without certain parameters. In addition, conversational threads can further increase in efficiency through experience based on user queries for data, as well as by providing training to the system (e.g., machine learning). During a training phase, providing additional synonyms for certain computer functions may also increase the efficiency of the conversational threads.

FIG. 13 illustrates an analysis query 1300 regarding access patterns for data analysis, consistent with an illustrative embodiment. Regarding patterns, there can be, for example, conversation patterns, analysis patterns and operation patterns.

DA conversation patterns are learned from prior DA workloads and application logs. Each of the conversation patterns is modeled as an intent in the conversation space and requires the generation of training examples.

DA Analysis patterns allow a user to see a measure sliced along a particular qualifying or categorical attribute, and may optionally have a filter applied. ADA Analysis query 1305 includes in this example a set of measure (M), a set of dimensions (D), and a set of filters (V). The utterance "Show me {M} by {D} for {V}" in an example can be "Show me admits (@Measure) by % Medical Diagnostic Code (MDC is the Dimension) for 2017 (Instance for dimension @year). It is to be understood that the present disclosure is not limited to the use of measures and dimensions, and that extracted quantifiable and qualifying or categorical attributes to entities for one or more parameters in an identified DA pattern can be used.

An example of other standard DA patterns 1307 include drill-down, roll up, and pivot. Drill-down accesses more granular information by adding dimensions to a current query. Roll up accesses higher-level information by aggregating along the dimension hierarchy, and pivot operation is accessing different information by replacing dimensions in the current query.

A ranking pattern 1309 allows for ordering the results by a measured value to obtain, for example, the top k values. In addition, DA comparison patterns 1311 allow comparison of two or more measures against each other along a particular dimension, and may optionally include a filter value. In the example shown, there is a comparison of hospital decisions by C-Section versus natural delivery by a hospital facility.

Example Processes

Figure 14:
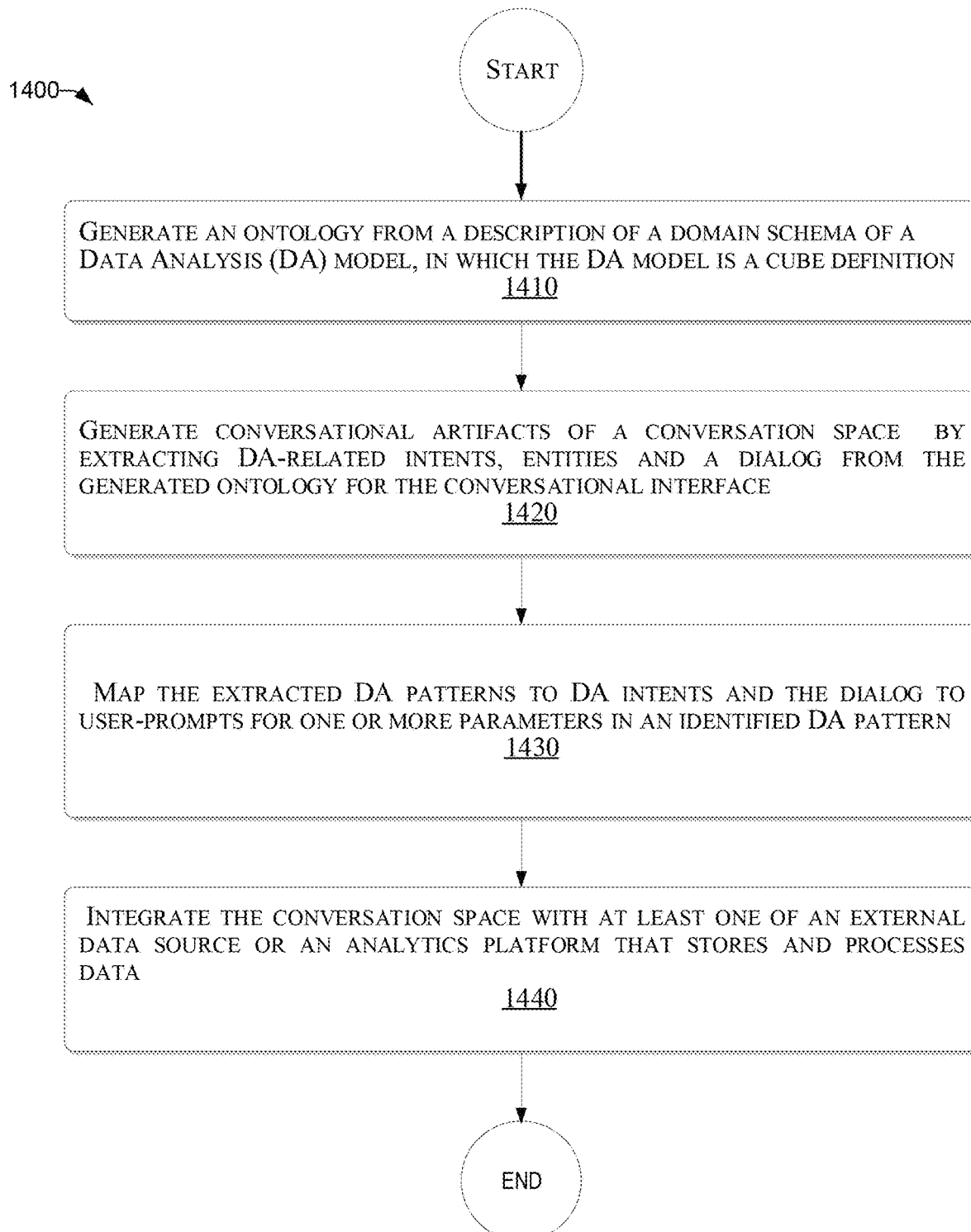
FIG. 14 depicts a flowchart of a conversational DI analysis, consistent with an illustrative embodiment.

With the foregoing overview of the example architecture, it may be helpful now to consider a high-level discussion of example processes. To that end, in conjunction with FIGS. 1 and 4, FIG. 14 illustrates a flowchart 1400 of a computer-implemented method for an ontology-driven conversational interface, consistent with an illustrative embodiment.

At operation 1410, the conversational interface generates an ontology from a description of a domain schema of a Data Analysis (DA) model, in which the DA model is a cube definition defined in terms of quantifiable, qualifying or categorical entities and their relationships as described by the domain schema. FIG. 4 shows a data model 401 (a cube definition).

At operation 1420, the conversational interface generates conversational artifacts of a conversation space including a conversational pattern framework by extracting DA-related intents, entities and a dialog from the generated ontology for the conversational interface. The conversation space, as shown in FIG. 4, the intents, entities, and a dialog, all of which permit communication with users.

At operation 1430, there is a mapping (see FIG. 5) to a dialog logic table of the extracted DA-related intents to DA patterns, extracted entities to quantifiable entities and the qualifying or categorical attributes, and the dialog to user-prompts for one or more parameters in an identified DA pattern.

At operation 1440, there is an integration of a conversational context of the conversational space with at least one of an external data source or an analytics platform that stores and processes data. This integration may be achieved through a structured query generation against the analytics platform to enable the conversation system to be able to respond to user utterances with insights such as charts and visualization. The process in this illustrative embodiment ends after operation 1440.

Figure 15:
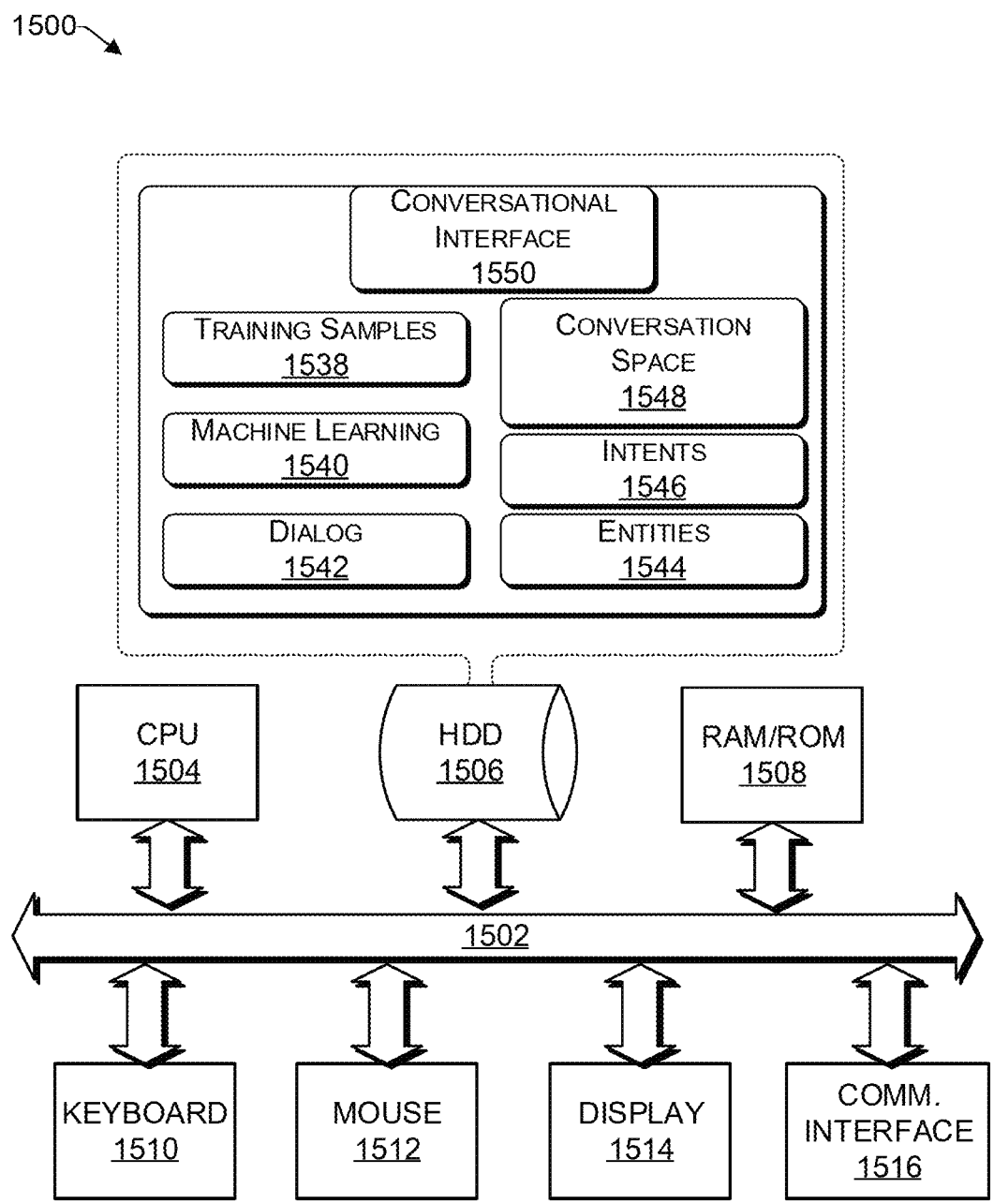
FIG. 15 is a functional block diagram illustration of a computer hardware platform that can communicate with various networked components, consistent with an illustrative embodiment.

FIG. 15 provides a functional block diagram illustration 1500 of a computer hardware platform. In particular, FIG. 15 illustrates a particularly configured network or host computer platform 1500, as may be used to implement the method for leveraging simple model predictions for enhancing performance shown in FIG. 4.

The computer platform 1500 may include a central processing unit (CPU) 1504, a hard disk drive (HDD) 1506, random access memory (RAM) and/or read-only memory (ROM) 1508, a keyboard 1510, a mouse 1512, a display 1514, and a communication interface 1516, which are connected to a system bus 1502. The HDD 1506 can include data stores.

In one embodiment, the HDD 1506, has capabilities that include storing a program that can execute various processes, such as for executing a conversational interface 1550, in a manner described herein. The conversational interface 1550 includes a conversation space 1548 including an intents module 1546, an entities module 1544, and a dialog 1542. There can be various modules configured to perform different functions that can vary in quantity.

For example, a training sample module 1538 stores various data to train the conversational space 1548 via a machine learning module 1540 configured to perform machine learning regarding utterances, and learning the intent of new or updated utterances.

In one embodiment, a program, such as Apache™, can be stored for operating the system as a Web server. In one embodiment, the HDD 1506 can store an executing application that includes one or more library software modules, such as those for the Java™ Runtime Environment program for realizing a JVM (Java™ virtual machine).

Example Cloud Platform

Figure 16:
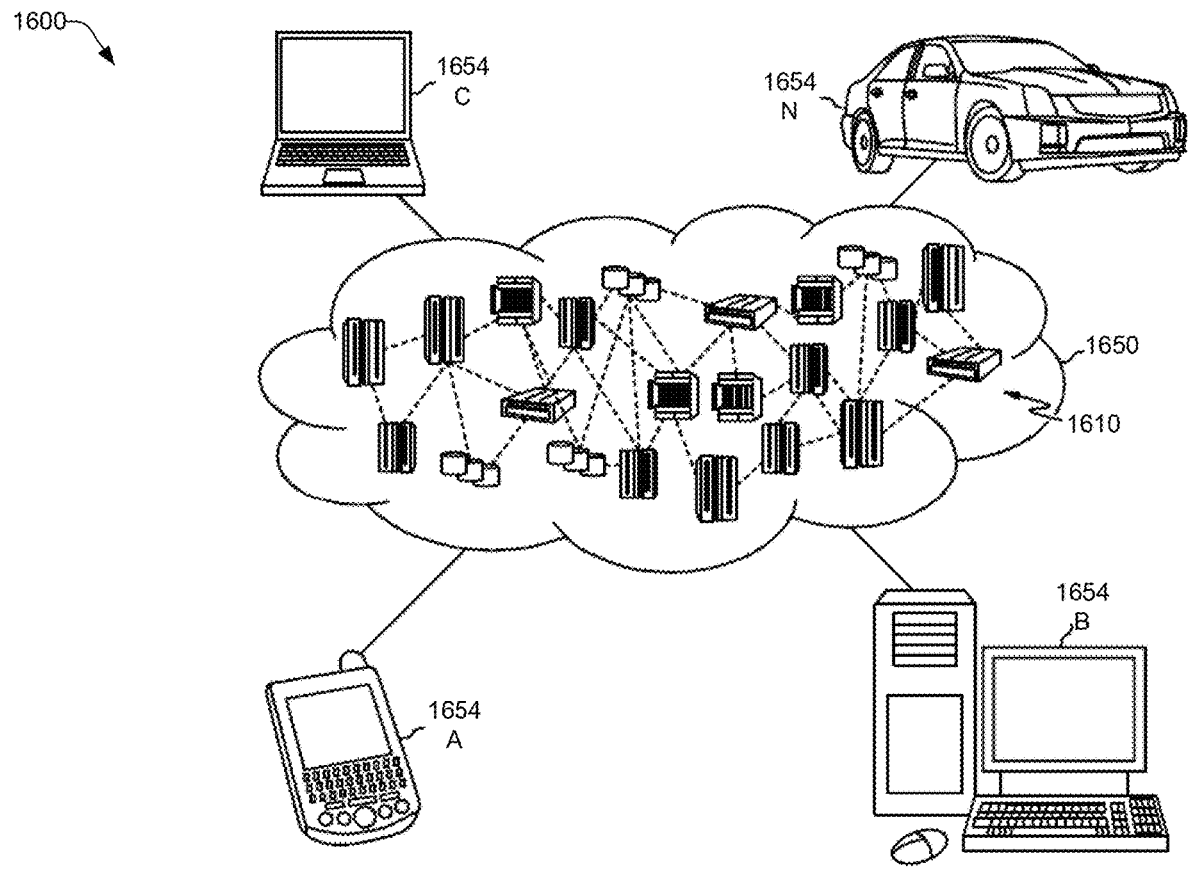
FIG. 16 depicts an illustrative cloud computing environment utilizing cloud computing.

As discussed above, functions relating to environmental and ecological optimization methods may include a cloud 1650 (see FIG. 16). It is to be understood that although this disclosure includes a detailed description of cloud computing as discussed hereinbelow, implementation of the teachings recited herein is not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service-oriented with a focus on statelessness, low coupling, modularity, and semantic interoperability. At the heart of cloud computing is an infrastructure that includes a network of interconnected nodes.

Referring now to FIG. 16, an illustrative cloud computing environment 1600 utilizing cloud computing is depicted. As shown, cloud computing environment 1600 includes cloud 1600 having one or more cloud computing nodes 1610 with which local computing devices used by cloud consumers, such as, for example, personal digital assistant (PDA) or cellular telephone 1654A, desktop computer 1654B, laptop computer 1654C, and/or automobile computer system 1654N may communicate. Nodes 1610 may communicate with one another. They may be grouped (not shown) physically or virtually, in one or more networks, such as Private, Community, Public, or Hybrid clouds as described hereinabove, or a combination thereof. This allows cloud computing environment 1600 to offer infrastructure, platforms, and/or software as services for which a cloud consumer does not need to maintain resources on a local computing device. It is understood that the types of computing devices 1654A-N shown in FIG. 16 are intended to be illustrative only and that computing nodes 1610 and cloud computing environment 1650 can communicate with any type of computerized device over any type of network and/or network addressable connection (e.g., using a web browser).

Figure 17:
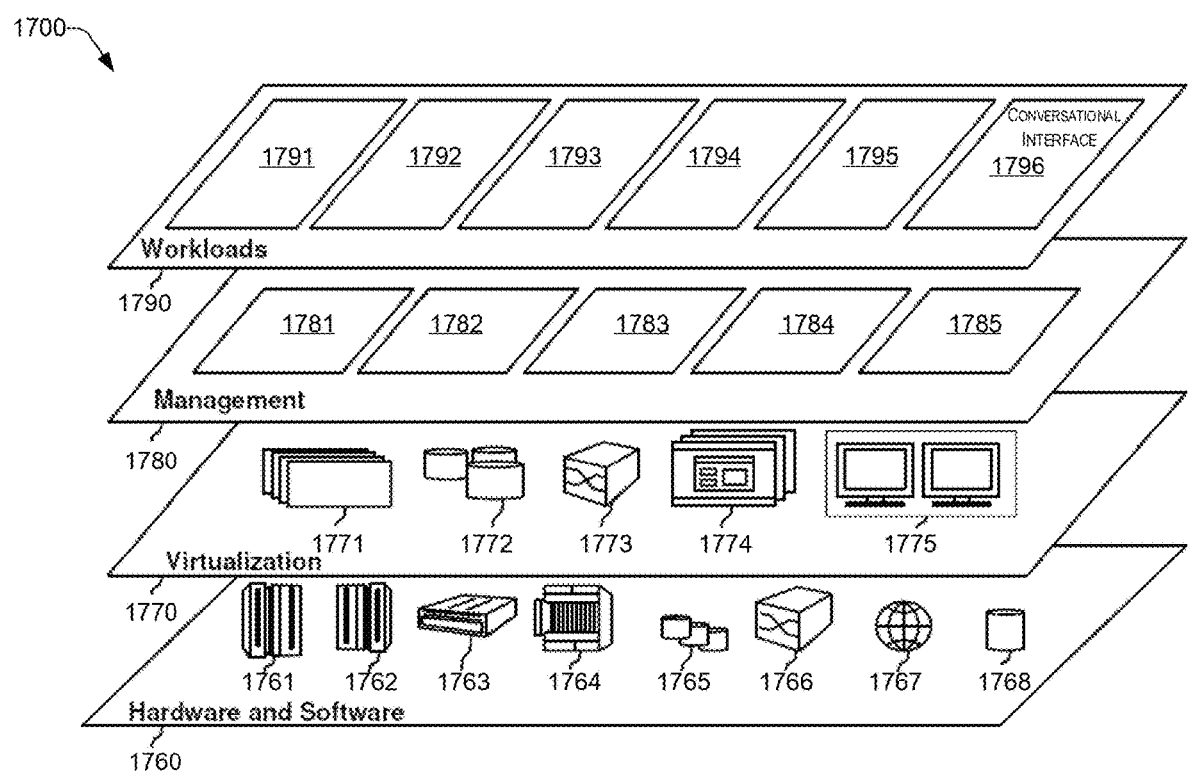
FIG. 17 depicts a set of functional abstraction layers provided by a cloud computing environment.

Referring now to FIG. 17, a set of functional abstraction layers 1700 provided by cloud computing environment 1600 (FIG. 16) is shown. It should be understood in advance that the components, layers, and functions shown in FIG. 17 are intended to be illustrative only and embodiments of the disclosure are not limited thereto. As depicted, the following layers and corresponding functions are provided:

Hardware and software layer 1760 include hardware and software components. Examples of hardware components include: mainframes 1761; RISC (Reduced Instruction Set Computer) architecture based servers 1762; servers 1763; blade servers 1764; storage devices 1765; and networks and networking components 1766. In some embodiments, software components include network application server software 1767 and database software 1768.

Virtualization layer 1770 provides an abstraction layer from which the following examples of virtual entities may be provided: virtual servers 1771; virtual storage 1772; virtual networks 1773, including virtual private networks; virtual applications and operating systems 1774; and virtual clients 1775.

In one example, management layer 1780 may provide the functions described below. Resource provisioning 1781 provides dynamic procurement of computing resources and other resources that are utilized to perform tasks within the cloud computing environment. Metering and Pricing 1782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1783 provides access to the cloud computing environment for consumers and system administrators. Service level management 1784 provides cloud computing resource allocation and management such that required service levels are met. Service Level Agreement (SLA) planning and fulfillment 1785 provide pre-arrangement for, and procurement of, cloud computing resources for which a future requirement is anticipated in accordance with an SLA.

Workloads layer 1790 provides examples of functionality for which the cloud computing environment may be utilized. Examples of workloads and functions which may be provided from this layer include: mapping and navigation 1791; software development and lifecycle management 1792; virtual classroom education delivery 1793; data analytics processing 1794; transaction processing 1795; and a conversational space module 1796 to perform calculating a similarity between graph-structured objects, as discussed herein.

Conclusion

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits, and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

The flowchart, and diagrams in the figures herein illustrate the architecture, functionality, and operation of possible implementations according to various embodiments of the present disclosure.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any such actual relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim.

Rather, as the following claims reflect, the inventive subject matter lies in less than all features of a single disclosed embodiment. Thus, the following claims are hereby incorporated into the Detailed Description, with each claim standing on its own as a separately claimed subject matter.

What is claimed is:

1. A computer-implemented method for generating an ontology-driven conversational interface, the method comprising:
   generating an ontology from a description of a domain schema of a Data Analysis (DA) model, in which the DA model is defined in terms of quantifiable, qualifying or categorical entities and their relationships as described by the domain schema;
   generating conversational artifacts of a conversation space by extracting DA-related intents, entities, and elements in building a dialog from the generated ontology for the conversational interface;
   mapping the extracted DA-related intents to DA patterns, the extracted entities to quantifiable and qualifying or categorical attributes and the dialog to agent-prompts for one or more parameters in an identified DA pattern of the DA patterns; and
   integrating the conversation space with at least one external data source or an analytics platform that stores and processes data.

2. The computer-implemented method according to claim 1, further comprising transmitting, by the conversational interface, a natural language response to a natural language query to access information in the external data source described by the DA model.

3. The computer-implemented method according to claim 1, further comprising retrieving data and visualizations from the analytics platform by the conversation space.

4. The computer-implemented method according to claim 1, further comprising providing meta-concepts as groupings of one or more of the quantifiable and qualifying or categorical attributes.

5. The computer-implemented method according to claim 1, further comprising:
   forming a dialog logic table by specifying one or more parameters associated with each intent; and
   identifying each of the specified one or more parameters as optional or required.

6. The computer-implemented method according to claim 5, wherein the dialog logic table is formed by specifying for each intent, natural language utterances of a user corresponding to the intent.

7. The computer-implemented method according to claim 1, wherein the conversation space includes one or more training samples for each intent, and the method further comprises training the conversational interface by machine learning to learn a model to identify an intent in a user utterance.

8. The computer-implemented method according to claim 7, wherein the training of the conversational interface is performed by a classification mechanism.

9. A computer-implemented method of generating a conversation space of a conversational interface for a Data Analysis (DA) application, the method comprising:
   generating an ontology from a description of a domain schema of a DA model described in terms of DA-related quantifiable and qualifying or categorical attributes as entities and relationships between them;
   annotating the ontology with semantic information from the DA model;

mapping of DA-related intents and entities extracted from the ontology to a dialog logic table, the dialog logic table including a quantifiable entity, a categorical attribute, a filter, and a relationship of mapped components;

generating one or more conversational artifacts of the conversation space from the ontology in terms of intents and entities and in building a dialog for the conversational interface; and integrating the conversation space with at least one of an external data source or analytics platform to store and process data.

10. The computer-implemented method according to claim 9, further comprising grouping of the entities from the ontology into one or more meta-concepts and a domain-dependent interpretation of each meta-concept.

11. The computer-implemented method according to claim 9, further comprising:

forming an ontology graph from the generated ontology;

enhancing the ontology graph by adding one or more of new concepts, groupings, hierarchies, relationships discerned from a data-driven machine learning, a deep learning, an embedding based technique for a named entity recognition, or a link prediction; and periodically enhancing the ontology graph and a subsequent process of generating the conversational artifacts as more data is consumed.

12. The computer-implemented method according to claim 9, further comprising adding a set of generic terms to the conversational space as synonyms for entities in user utterances.

13. The computer-implemented method according to claim 9, wherein generating the ontology further comprises obtaining a taxonomy or hierarchies from a domain description of the DA model in terms of parent-child relationships.

14. The computer-implemented method according to claim 9, further comprising:

configuring a generic dialog structure for making a series of complex open requests for one or more DA-related requests including one or more of analytic queries, trend requests and comparison requests.

15. The computer-implemented method according to claim 9, wherein a set of generic operations for one or more DA-related requests is configured for DA, and includes operations for drill down, roll up, and a pivot on a previous query.

16. The computer-implemented method according to claim 9, further comprising integrating one or more DA-related requests and operations with a Natural Conversation Space, which includes a persistent context, natural conversation activities and conversation management actions.

17. An ontology-driven conversational interface of a conversation device, comprising:

an intent module configured to identify goals and actions from utterances received from a user as one or more intents;

an entity module configured to identify information associated with a user intent as one or more entities;

a dialog module configured to provide a response to the user based on the identified one or more intents, the identified one or more entities, and a context of a conversation;

a processor configured to:

generate an ontology from a description of a domain schema of a Data Analysis (DA) model; and generate one or more conversational artifacts of a conversation space by extracting DA-related intents, entities and elements in building a dialog from the generated ontology for the conversational interface; and an analytics platform configured to store and process data that the conversation space returns to the user, and to provide one or more responses to user queries generated through structured queries in a form of at least one of charts, visualizations, or audio, wherein the ontology includes at least one meta-concept as a grouping of one or more of quantifiable or qualifying or categorical attributes associated with the extracted entities of the generated ontology.

18. The conversational interface according to claim 17, wherein the DA model is defined in terms of quantifiable, qualifying or categorical entities and their relationships as described by the domain schema, and the conversational interface further comprises:

a training module configured to train for identification of different types of user intent from one or more training samples including user utterances.

19. The conversational interface according to claim 17, wherein the processor is further configured to:

form an ontology graph from the generated ontology;

enhance the ontology graph by adding one or more of new concepts, groupings, hierarchies, relationships discerned from a data-driven machine learning, a deep learning, an embedding based technique for a named entity recognition, or a link prediction; and periodically enhance the ontology graph and subsequent process of generating the artifacts as more data is consumed.

20. The conversational interface according to claim 17, wherein the analytics platform comprises a healthcare analysis platform or a finance platform.

21. A non-transitory computer-readable storage medium tangibly embodying a computer-readable program code having computer-readable instructions that, when executed, causes a computer device to perform a method for generating an ontology-driven conversational interface, the method comprising:

generating an ontology from a description of a domain schema of a Data Analysis (DA) model, wherein the DA model is defined in terms of quantifiable, qualifying or categorical entities and their relationships as described by the domain schema;

generating conversational artifacts of a conversation space by extracting DA-related intents, entities and elements in building a dialog from the generated ontology for the conversational interface;

receiving by the conversational interface, a natural language query to access information in an external data source described by the DA model; and transmitting, by the conversational interface, a natural language response to the natural language query.

22. The computer-readable storage medium according to claim 21, wherein the method further comprises:

in response to receiving the natural language query to access information in the external data source described by the DA model, parsing the natural language query to extract query entities and query intents from the natural language query;

generating a plurality of query responses to the natural language query based upon the query extracted intents and entities; and ranking the query responses, wherein the transmitting of the natural language response comprises a top-ranked query response to the natural language query.

23. The computer-readable storage medium according to claim 21, wherein the method further comprises:
- mapping of the extracted DA-related intents to DA-patterns, the extracted entities to quantifiable and qualifying or categorical attributes, and the dialog to user-prompts for one or more parameters in an identified DA pattern of the DA patterns;
- integrating the conversation space with at least one of the external data source or an analytics platform that stores and processes data; and
- forming a dialog logic table by specifying for each intent, natural language utterances of a user corresponding to the intent.

24. The computer-readable storage medium according to claim 23, wherein the method further comprises:
- providing at least one meta-concept as a grouping of one or more of the quantifiable and qualifying or categorical attributes; and
- annotating the ontology with semantic information from the DA model.

25. A non-transitory computer-readable storage medium tangibly embodying a computer-readable program code having computer-readable instructions that, when executed, causes a computer device to perform a method for generating an ontology-driven conversational interface, the method comprising:
- generating an ontology from a description of a domain schema of a Data Analysis (DA) model, in which the DA model is defined in terms of quantifiable, qualifying or categorical entities and their relationships as described by the domain schema;
- generating conversational artifacts of a conversation space by extracting DA-related intents, entities, and elements in building a dialog from the generated ontology for the conversational interface;
- using a default inference to provide one or more missing parameters in a query based on the extracted DA-related intents, entities, and elements;
- mapping the extracted DA-related intents to DA patterns, the extracted entities to quantifiable and qualifying or categorical attributes and the dialog to agent-prompts for one or more parameters in an identified DA pattern of the DA patterns; and
- integrating the conversation space with at least one external data source or an analytics platform that stores and processes data.

* * * * *